(12) United States Patent
Lam et al.

(10) Patent No.: US 8,076,528 B2
(45) Date of Patent: Dec. 13, 2011

(54) PRESSURE SENSITIVE ADHESIVE COMPOSITION COMPRISING CROSS-LINKED POLYALKYLENE OXIDE AND WATER ABSORBENT HYDROPHILIC AGENTS

(75) Inventors: Peter Kwok Hing Lam, Frederiksberg C (DK); Kristoffer Hansen, Maaloev (DK); Anders Bach, Copenhagen S (DK); Mads Lykke, Broenshoej (DK)

(73) Assignee: Coloplast A/S, Humlebaek (DK)

( * ) Notice: Subject to any disclaimer, the term of this patent is extended or adjusted under 35 U.S.C. 154(b) by 440 days.

(21) Appl. No.: 12/227,016

(22) PCT Filed: May 3, 2007

(86) PCT No.: PCT/DK2007/050055
§ 371 (c)(1),
(2), (4) Date: Mar. 12, 2009

(87) PCT Pub. No.: WO2007/128320
PCT Pub. Date: Nov. 15, 2007

(65) Prior Publication Data
US 2009/0306571 A1 Dec. 10, 2009

(30) Foreign Application Priority Data
May 5, 2006 (DK) ................................. 2006 00634

(51) Int. Cl.
*A61F 13/00* (2006.01)
*C08G 18/38* (2006.01)
*C08L 83/00* (2006.01)

(52) U.S. Cl. ................. 602/56; 602/52; 602/54; 524/35; 524/588

(58) Field of Classification Search ............... 602/41–59; 524/35, 588
See application file for complete search history.

(56) References Cited

U.S. PATENT DOCUMENTS

| | | | |
|---|---|---|---|
| 5,054,488 A | 10/1991 | Muz | |
| 5,086,764 A | 2/1992 | Gilman | |
| 5,458,124 A | 10/1995 | Stanko et al. | |
| 5,643,187 A | 7/1997 | Naestoft et al. | |
| 6,162,456 A | 12/2000 | Dunbar et al. | |
| 6,248,915 B1 | 6/2001 | Ito et al. | |
| 6,372,951 B1 | 4/2002 | Ter-Ovanesyan et al. | |
| 6,385,473 B1 | 5/2002 | Haines et al. | |
| 2003/0009097 A1 | 1/2003 | Sheraton et al. | |

FOREIGN PATENT DOCUMENTS

| | | |
|---|---|---|
| EP | 0 236 104 A2 | 9/1987 |
| EP | 0 641 553 A1 | 3/1995 |
| JP | 2002 224706 A | 8/2002 |
| JP | 2004 067720 A | 3/2004 |
| WO | WO 91/01706 | 2/1991 |
| WO | WO 98/55157 | 12/1998 |
| WO | WO 99/59465 | 11/1999 |
| WO | WO 02/05737 A1 | 1/2002 |
| WO | WO 02/06687 A1 | 1/2002 |
| WO | WO 02/087642 A2 | 11/2002 |
| WO | WO 02/087645 A1 | 11/2002 |
| WO | WO 03/065926 A2 | 8/2003 |
| WO | WO 2005/021058 A2 | 3/2005 |
| WO | WO 2005/032401 A2 | 4/2005 |
| WO | WO 2005/032610 A1 | 4/2005 |

OTHER PUBLICATIONS

Main, K., et al., "Influence of Sex and Growth Hormone Deficiency on Sweating," Scand. J. Clin. Lab Invest. vol. 51, pp. 475-480, 1991.

*Primary Examiner* — Kim Lewis
(74) *Attorney, Agent, or Firm* — Jacobson Holman PLLC

(57) ABSTRACT

Accordingly, the present invention relates to a pressure sensitive adhesive composition consisting of a continuous phase comprising cross-linked polyalkyleneoxide polymer and a discontinuous phase comprising water absorbent hydrophilic agents wherein
a) the water absorbent hydrophilic agent(s) is present in an amount between 1 and 40% w/w of the total adhesive composition; and
b) the continuous phase comprises the reaction product (X) of:
  (i) a polyalkyleneoxide polymer having one or more unsaturated end groups, and where more than 90% w/w of the polyalkylene oxide polymer consist of polymerised alkyleneoxide moities having three or more carbon atoms, and
  (ii) an organosiloxane comprising one or more Si—H groups,
carried out in the presence of an addition reaction catalyst. The present invention also relates to medical devices comprising such pressure sensitive adhesives.

38 Claims, No Drawings

US 8,076,528 B2

PRESSURE SENSITIVE ADHESIVE COMPOSITION COMPRISING CROSS-LINKED POLYALKYLENE OXIDE AND WATER ABSORBENT HYDROPHILIC AGENTS

This is a national stage of PCT/DK07/050,055 filed May 3, 2007 and published in English, which has a priority of Denmark no. PA 2006 00634 filed May 5, 2006, hereby incorporated by reference.

FIELD OF THE INVENTION

The present invention relates to a novel pressure sensitive adhesive composition comprising cross-linked polyalkyleneoxide polymer and water absorbent hydrophilic agents, and medical devices comprising said pressure sensitive adhesive composition.

BACKGROUND OF THE INVENTION

Pressure sensitive adhesives have for a long time been used for attaching medical devices, such as ostomy appliances, dressings (including wound dressings), wound drainage bandages, devices for collecting urine, orthoses and prostheses to the skin.

It has been reported that humans for short periods can sweat more than 20,000 g/m2/24 h, see Main, K., K. O, Nilsson, and N. E. Skakkebaek, 1991, Influence of sex and growth hormone deficiency on sweating, Scand. J. Clin. Lab Invest 51:475-480.

Thus, the moisture handling ability of skin contact adhesives, i.e. both the water absorption capacity and the moisture vapour transmission rate of the adhesive, is important.

Pressure sensitive adhesives with high water vapour transmission, which are suitable for skin contact use, have been described in WO 2005/032401. The pressure sensitive adhesive composition described in this patent application is the reaction product of a polypropylene oxide having at least two unsaturated end groups and a polysiloxane cross-linking agent comprising Si—H groups. This application suggests the incorporation of water-soluble polymer or absorptive polymers into the adhesive but there are no details or examples as regards the amount or kind of water-soluble polymer or absorptive polymer to be incorporated into the adhesive. Also there is no clear description of the effect of the addition of water-soluble polymers or absorptive polymers have on the adhesive.

In the polyalkyleneoxide polymer for the continuous phase of the adhesive according to the present invention, more than 90% w/w of the polyalkyleneoxide polymer consist of polymerized alkyleneoxide moieties having three or more carbon atoms and even though the polyalkyleneoxide is hydrophobic, it has very good moisture vapour transmission rate. Being hydrophobic, the polyalkyleneoxide used for the continuous phase of the adhesive according to the present invention have, as such, a low water absorption capacity.

Hydrocolloids has for a long time been added to pressure sensitive adhesives, such as adhesives based on thermoplastic elastomers, in order to impart wet tack and moisture absorbent properties to the adhesive.

However, it is well known that retention of moisture in hydrocolloid adhesives may cause changes in the adhesive, such as swelling, loss of cohesion, loss of adhesion, and erosion or disintegration of the adhesive.

Furthermore, addition of hydrocolloids to adhesives increases the moduli of the adhesive, making the adhesive less skin friendly, harder and less comfortable to wear.

It has now been found, that a surprisingly high increase in water vapour permeability and water absorption capacity may be achieved by adding an amount of water absorbent hydrophilic agent that does not compromise the softness and the erosion resistance of the adhesives of the invention.

SUMMARY OF THE INVENTION

Accordingly, the present invention relates to a pressure sensitive adhesive composition consisting of a continuous phase comprising cross-linked polyalkyleneoxide polymer and a discontinuous phase comprising water absorbent hydrophilic agents wherein
a) the water absorbent hydrophilic agent(s) is present in an amount between 1 and 40% w/w of the total adhesive composition; and
b) the continuous phase comprises the reaction product (X) of:
  (i) a polyalkyleneoxide polymer having one or more unsaturated end groups, and wherein more than 90% w/w of the polyalkylene oxide polymer consist of polymerised alkyleneoxide moities having three or more carbon atoms, and
  (ii) an organosiloxane comprising one or more Si—H groups,
 carried out in the presence of an addition reaction catalyst.

The present invention also relates to medical devices comprising such pressure sensitive adhesives.

DETAILED DESCRIPTION OF THE INVENTION

As used herein, the total adhesive composition means the discontinuous phase and the continuous phase in combination.

As used herein the discontinuous phase means the solid materials, preferably in particulate form, which is distributed in the continuous phase. The water absorbent hydrophilic agent is part of the discontinuous phase.

As used herein the continuous phase is the adhesive composition, corresponding to the total adhesive composition minus the discontinuous phase.

Whenever a figure for moisture vapour transmission rate of an adhesive composition is given herein it is the moisture vapour transmission rate measured according to example 3 below.

Whenever a figure for the water absorption of an adhesive composition is given herein it is the water absorption measured according to example 3 below.

Whenever a figure for the erosion of an adhesive composition is given herein, it is the erosion measured according to example 5 below.

The term embedded means that all sides of the one or more element(s) is covered by the adhesive body of the composition of the invention or where the one or more element(s) is placed in a recess or cavity in the adhesive body of the composition of the invention, and is accessible from the outside.

According to one embodiment of the invention, the continuous phase comprises the reaction product (Y) of:
  (ia) a polyalkyleneoxide polymer having at least two unsaturated end groups, and wherein more than 90% w/w of the polyalkylene oxide polymer consist of polymerised alkyleneoxide moities having three or more carbon atoms, (iia) a polysiloxane cross-linking agent comprising 3 or more Si—H groups and optionally (iiia) a polysiloxane chain extender comprising up to 2 Si—H groups, carried out in the presence of an addition reaction catalyst.

According to a preferred embodiment of the invention, the continuous phase of the pressure sensitive adhesive is an adhesive as described in WO 05/032401.

According to a preferred embodiment of the invention, the polyalkyleneoxide polymer having one or more unsaturated end groups is therefore polypropyleneoxide having one or more unsaturated end groups.

In one particular embodiment the continuous phase of the adhesive composition of the invention comprises the reaction product Z) of (ib) polypropylene oxide having at least two unsaturated end groups, (iib) a polysiloxane cross-linking agent comprising 3 or more Si—H groups and optionally (iiib) a polysiloxane chain extender comprising up to 2 Si—H groups, carried out in the presence of an addition reaction catalyst.

The continuous phase of the adhesive of the invention may comprise the above mentioned reaction products, as well as other ingredients, such as other polymers or polymeric reaction products.

In one preferred embodiment of the invention the continuous phase comprises at least 60% w/w, at least 70% w/w, at least 80% w/w, preferred at least 90% w/w, or more preferred at least 95% w/w, or most preferred at least 98% w/w of the above mentioned reaction products.

In a preferred embodiment the total adhesive composition comprises 5-40% w/w, more preferred 5-35% w/w, still more preferred 5-30% w/w, or most preferred 10-30% w/w of the water absorbent hydrophilic agent(s).

The polyalkylene oxide polymer having one or more unsaturated groups may be branched or linear.

However, suitably, the polyalkylene oxide polymer is linear and has two unsaturated end groups.

The polypropylene oxide having unsaturated end groups may be a compound of formula $$CH_2=C(R^1)-(Z)-O-(X)_n-(W)-C(R^2)=CH_2 \quad (Ia)$$

or $$CH(R^1)=CH-(Z)-O-(X)_n-(W)-CH=CH(R^2) \quad (Ib)$$

wherein
$R^1$ and $R^2$ are independently selected from hydrogen and $C_{1-6}$-alkyl;
Z and W is $C_{1-4}$-alkylene;
X is $-(CH_2)_3-O-$ or $-CH_2-CH(CH_3)-O-$; and
n is 15-900, more preferred 30-600, or most preferred 300-600.

The number average molecular weight of the polyalkylene oxide having unsaturated end groups is suitably between 1000 and 100000, more preferred between 2000 and 50.000 and most preferred between 17.000 and 35.000.

Polypropylene oxide having unsaturated end groups may be prepared as described in U.S. Pat. No. 6,248,915 and WO 05/032401 or analogously to the methods described therein. Other polyalkylene oxide polymers may be prepared analogously.

The polysiloxane cross-linking agent comprising 3 or more Si—H groups is suitable a compound having the formula $$R-SiO(R,R)-(SiO(R,R))_m-Si-(R,R,R) \quad (II)$$

wherein
at least three of the groups R is hydrogen and the rest of the groups R are each independently selected from $C_{1-12}$-alkyl, $C_{3-8}$-cycloalkyl, $C_{6-14}$-aryl, and $C_{7-12}$-arylalkyl; and
m is 10-50, or preferably 10-13. The number average molecular weight as determined by GPC is suitably 1000-3000.

One or more cross-linking agents of formula (II) may be used in the cross-linking reaction.

In one embodiment of the invention, a mixture of one or more cross-linking agents of formula (II) comprising 3 or more Si—H groups and a polysiloxane chain extender comprising up to 2 Si—H groups is used in the cross-linking reaction.

In a preferred embodiment of the invention, a mixture of one or more cross-linking agents of formula (II) comprising 3 or more Si—H groups and a polysiloxane chain extender comprising up to 2 Si—H groups is used in the cross-linking reaction, and wherein the average number of Si—H groups in the cross-linking agents and the chain extender are above 2.

The polysiloxane chain extender is suitably a compound having the formula $$R^3-SiO(R^3,R^3)-(SiO(R^3,R^3))_m-Si-(R^3,R^3,R^3) \quad (III)$$

wherein
up to 2 of the groups $R^3$ is hydrogen and the rest of the groups $R^3$ are each independently selected from $C_{1-12}$-alkyl, $C_{3-8}$-cycloalkyl, $C_{6-14}$-aryl, and $C_{7-12}$-arylalkyl; and
m is 0-50. The number average molecular weight as determined by GPC is suitably between 200 and 65000, most preferably between 200 and 17500.

As used herein $C_{1-12}$-alkyl means a linear or branched alkyl group having 1 to 12 carbon atoms, $C_{1-8}$-alkyl means a linear or branched alkyl group having 1 to 8 carbon atoms, and $C_{1-6}$-alkyl means a linear or branched alkyl group having 1 to 6 carbon atoms, such as methyl, ethyl, propyl, isopropyl, butyl, pentyl and hexyl.

As used herein $C_{1-4}$-alkylene means a linear or branched divalent alkylene group having 1 to 4 carbon atoms, such as methylene, ethylene, propylene, isopropylene, butylenes and isobutylene.

As used herein $C_{3-8}$-cycloalkyl means a cyclic alkyl group having 3-8 carbon atoms, such as cyclopentyl and cyclohexyl.

As used herein $C_{6-14}$-aryl means a phenyl or naphthyl group optionally substituted with $C_{1-6}$-alkyl, such as tolyl and xylyl.

As used herein $C_{7-12}$-arylalkyl means aryl attached to a $C_{1-6}$-alkyl group, where $C_{1-6}$-alkyl and aryl is as defined above, such as benzyl, phenethyl and o-methylphenethyl.

In the compound of formula (II) and in the compound of formula (III), the groups R and $R^3$, which are not hydrogen, are suitably each independently selected from a member of the group $C_{1-6}$-alkyl, $C_{6-14}$-aryl or $C_{7-12}$-arylalkyl.

The Si—H groups may be situated at either end of the compound of formula (II). However, at least one Si—H group is preferably positioned within the $-(SiO(R^3R^3))_m-$ chain of the compound of formula (II).

The polysiloxane cross-linking agent and the chain extender may be prepared as described in Japanese Patent Application 2002-224706 and WO 05/032401 or analogously to the methods described therein.

The reaction of the polyalkylene oxide having unsaturated end groups with the polysiloxane cross-linking agent and optionally a chain extender is suitably carried out in presence of a catalyst.

Suitable catalysts for the reaction are described in U.S. Pat. No. 6,248,915. Preferred catalysts are platinum-vinylsiloxan and platinum-olefin complexes, such as Pt-divinyl tetramethyl disiloxane.

The reaction is suitably carried out neat at a temperature between 25° C. and 150° C. It is not necessary to use a solvent for the reaction, which is an advantage in the preparation of any adhesive, but especially in the preparation of adhesives for skin applications.

Suitably, the ratio of the number of reactive Si—H groups in the polysiloxane cross-linking agent to the number of unsaturated groups in the polypropylene oxide, which are reactive with Si—H groups under the reaction conditions, is between 0.2 and 0.8.

The amount of polysiloxane used for the cross-linking is suitably less than 10% w/w, and more preferred below 5% w/w of the amount of polyalkylene oxide polymer having unsaturated end groups.

The cross-linking reaction does not lead to complete cross-linking of the all polyalkylene oxide polymers. The continuous phase comprises a mixture of cross-linked and non cross-linked polyalkylene oxide polymer.

Polypropylene oxide having at least two unsaturated end groups, which are useful according to the invention, may be obtained from the company Kaneka. ACX003 has been used in the experimental section below.

Polysiloxane cross-linking agent comprising 3 or more Si—H groups may also be obtained from the company Kaneka. CR600 has been used in the experimental section below.

Adhesives comprising a reaction product of ACX003 and CR600, wherein the weight percent of CR 600 is 5.0 w/w or below of the total weight of ACX003 and CR600, are particularly preferred.

The water absorbent hydrophilic agent is added to the reaction composition before the reactants are cross-linked.

The water absorbent hydrophilic agent is suitably a particulate, solid water absorbent hydrophilic agent.

The water absorbent hydrophilic agent may suitably be a water soluble or a water swellable (non-water soluble) hydrocolloid. The water soluble or water swellable (non-water soluble) hydrocolloids may suitably be selected from natural or synthetic hydrocolloids, such as guar gum, locust bean gum, pectin, alginates, gelatine, xantan or gum karaya, cellulose derivatives (e.g. salts of carboxymethyl cellulose such as sodium carboxymethyl cellulose, methyl cellulose and hydroxypropyl cellulose), sodium starch glycolate, polyvinylalcohol, polyacrylic acid (e.g. in the form of super absorbent particles SAP), and polyethylene glycol. Suitable hydrocolloids are e.g. AQ 1045 (a branched water dispersible polyester) from Eastman, Pectin LM 12CG Z or Pectin USP/100 from Copenhagen Pectin, Natrosol (hydroxyethyl cellulose, non-ionic, water soluble ethers of cellulose and ethylene oxide) produced by AQUALON, Blanose 9H4XF (carboxymethyl cellulose) available from Hercules, Akucell® AF 2881 (carboxymethyl cellulose) available from Akzo, Aqua-Sorb® (cross-linked carboxymethyl cellulose) from Aqualon, Sorbalg pH 470 (Calcium alginate) from Danisco Ingredients, Denmark.

One or more water absorbent hydrophilic agents, e.g. selected from the hydrocolloids mentioned above, may be included in the adhesive composition of the invention.

According to a preferred embodiment of the invention, the water absorbent hydrophilic agent is a water swellable (non water soluble) hydrocolloid. Suitably, the water absorbent hydrophilic agent comprises a cross linked hydrophilic polymer, such as cross-linked carboxymethyl cellulose.

The hydrocolloids may also be selected from microcolloids (e.g having a particle size less than 20 microns or preferably below 5 or 2 microns), such as those described in WO 02/06687.

The invention may be foamed before or during the cross-linking of the polyalkyleneoxide polymer polymer and cross-linked into foamed adhesive in a number of ways, either chemically or mechanically.

Chemical blowing agents or other materials added to the adhesive formula itself may generate gas bubbles by a variety of mechanisms. These mechanisms include but are not limited to chemical reaction, physical changes, thermal decomposition or chemical degradation, leaching of a dispersed phase, volatilisation of low boiling materials or by a combination of these methods.

Any of the commercially known chemical blowing agents may be used. The chemical blowing agents is suitably non-toxic, skin friendly, and environmentally safe, both before and after decomposition.

The amount of chemical blowing agent to be added to the adhesive mixture may range from about 0.01% up to about 90% by weight, with a practical range including about 1% up to about 20% by weight. The amount of gas to be added may be determined by measuring the amount of gas generated from a candidate mixture and calculating the amount of foaming required for the final product, tempered by experience of the amount of gas lost to atmosphere during the foaming process.

Another method for creating a foamed adhesive of the invention, is a method where a mechanical process is used to add a physical blowing agent, similar to whipping the adhesive mass into froth, thus creating a foamed structure. Many processes are possible including processes involving incorporation of air, nitrogen, carbon dioxide, or other gases or low boiling point volatile liquids during the manufacturing process for the adhesive as the cross-linking reaction takes place.

Another method for creating a foamed adhesive of the invention is by using a small amount of moisture in the hydrocolloid, which expands during the heating and cross-linking process.

The pressure sensitive adhesive used according to the invention may contain other conventional ingredients for adhesive compositions, such as tackifiers, extenders, non-reactive polymers, oils (e.g. polypropylenoxide, ethyleneoxide-propyleneoxide copolymers, mineral oil), plastizisers, fillers, surfactants. The adhesive may also comprise pharmaceutically active ingredients. These optional ingredients may be present in the reaction mixture during the cross linking reaction.

The invention also relates to medical devices comprising a pressure sensitive adhesive composition as described above.

The medical device comprising an adhesive composition according to the invention may be an ostomy appliance, a dressing (including wound dressings), a wound drainage bandage, a skin protective bandage, a device for collecting urine, an orthose or a prosthese, and electronic device such as a measuring instrument or a power source, such as a battery.

The medical device may also be a tape (e.g an elastic tape or film) or a bandage, for securing a medical device, or a part of the medical device to the skin, or for sealing around a medical device attached to the skin.

The medical device may in its simplest construction be an adhesive construction comprising a layer of the pressure sensitive adhesive composition according to the invention and a backing layer.

The backing layer is suitably elastic (have a low modulus), enabling the adhesive construction to conform to the skin movement and provide comfort when using it.

The thickness of the backing layer used according to the invention is dependent on the type of backing used. For polymer films, such as polyurethane films, the overall thickness may be between 10 to 100 μm, preferably between 10 to 50 μm, most preferred about 30 μm.

In one embodiment of the invention the backing layer is non-vapour permeable. In this case the adhesive construction of the invention may provide good moisture absorption rate and absorption capacity.

In another embodiment of the invention the backing layer is water vapour permeable and have a moisture vapour transmission rate above 500 g/m$^2$/24 h. In this case the adhesive construction of the invention may provide a good moisture absorption rate and absorption capacity and is able to transport a large quantity of moisture through the construction and away from the skin. Both the chemical composition and physical construction of the adhesive layer and the chemical and physical construction of the backing layer affect the water vapour permeability. With regard to the physical construction, the backing layer may be continuous (no holes, perforations, indentations, no added particles or fibers affecting the water vapour permeability) or discontinuous (it has holes, perforations, indentations, added particles or fibers affecting the water vapour permeability).

When the backing layer is water vapour permeable, the permeability thereof is preferably considerably higher than for the adhesive layer.

The moisture vapour transmission rate of the backing layer is suitably above 500 g/m$^2$/24 h, most preferably above 1000 g/m2/24 h, even more preferred above 3000 and most preferred above 10.000.

Suitable materials for backing layers include water vapour permeable polyurethane, polyethylene, polybutadiene, polyvinyl chloride, polyvinylidene chloride, polyvinyl alcohol, polyacrylate, polysulphone, polystyrene, polypropylene, polyamide, ethylene-vinylacetate copolymer, polyester, polycarbonate, polyvinyl fluoride, copolyester ether, synthetic or natural rubbers, silicones and mixtures of these. Particularly preferred are elastomers, such as polyurethane, polyethers and synthetic or natural rubbers. The backing layer may also be a woven or non-woven material or a foam.

The backing layer may consist of more than one layer.

In one embodiment the backing material is weldable.

In a special embodiment of the invention, the layer shows higher vapour permeability when in contact with liquid.

The backing layer is preferably a low-friction flexible polymer film, and suitably an elastic material. A suitable material for use as a water impervious film is a polyurethane film and a preferred low friction film material is disclosed in U.S. Pat. No. 5,643,187.

The backing may be attached to the adhesive layer by the adhesive properties of the adhesive or more preferred by casting the reaction mixture onto the backing layer and then curing (e.g. at elevated temperature).

In order to improve the adhesion of the backing layer to the adhesive layer, the backing layer may be pretreated, e.g. by corona, flame, chemical or plasma treatment. Where the backing layer is a polyurethane film the preferred treatment is treatment with an adhesive promoter, such as CFI-135 available from Nusil.

The adhesive may cover one surface of a backing layer entirely or may be applied in a pattern in a manner known per se for applying an adhesive onto a backing, e.g. screen printing, gravure, or spraying.

The pressure sensitive adhesives according to the invention have a very high moisture vapour transmission rate, which makes them breathable and very skin friendly. The high moisture transmission of these adhesives is a particular advantage where a medical device has to be worn on the skin for a long time, e.g. days.

The preferred content of water absorbent hydrophilic agent in the adhesive composition of the invention has been found to be highly dependent on the particular use of the adhesive composition/medical device.

For some medical devices it is important that the adhesive has high moisture vapour transmission rate, whereas the water absorption capacity is less important. This is the case with very thin dressings (e.g. for use on the face), wound dressings having an absorbent element or pad incorporated into the dressing, skin protective dressings used over skin where there are no cuts or wounds, etc.

For these uses, the adhesive preferably has a high moisture vapour transmission rate but does not necessarily need to have a high absorption capacity. A certain water absorption capacity may function as a buffer in case of severe sweating. However, a high water absorption capacity also makes the water resistance of the adhesive lower, e.g. during washing or showering. Absorption of exudates from a wound may be handled by a separate absorbent element and the moisture vapour transmission rate of the adhesive is therefore in many cases more important than water absorption capacity.

As may be seen from the experimental part below, the softness of the adhesive of the invention decreases dramatically from 30 to 40% w/w of water absorbent hydrophilic agent.

According to one embodiment, the invention therefore relates to a dressing (for example very thin dressings for use on the face, wound dressings having an absorbent element or pad incorporated into the dressing, skin protective dressings used over skin where there are no cuts or wounds, etc.), which comprises an adhesive composition of the invention where the amount of water absorbent hydrophilic agent(s) in the adhesive composition is between 5 and 30% w/w, preferably between 10 and 30% w/w, more preferred between 10 and 20% w/w, or between 10 and 15% w/w. According to another embodiment the amount of water absorbent hydrophilic agent(s) in the adhesive composition is between or between 5 and 25% w/w, or between 5 and 15% w/w, or between 5 and 10% w/w. The backing layer for such dressings is suitably selected from elastic backing layers having a higher moisture vapour transmission rate than the adhesive layer.

Thus, according to one embodiment, the invention relates to a medical device, e.g. a dressing, comprising the adhesive composition of the invention in the form of a layer attached to a backing and wherein the adhesive composition comprises 5-30% w/w, preferably 10-30% w/w, or most preferred 10-20% w/w of water absorbent hydrophilic agent(s) and the backing layer has a moisture vapour transmission rate above 500 g/m$^2$/24 h.

According to another embodiment, the invention relates to a medical device, e.g. a dressing, comprising the adhesive composition of the invention in the form of a layer attached to a backing and wherein the adhesive composition comprises 5-25% w/w, preferably 5-15% w/w, or between 5 and 10% w/w of water absorbent hydrophilic agent(s) and the backing layer has a moisture vapour transmission rate above 500 g/m$^2$/24 h.

According to a further embodiment, the invention relates to a medical device as above, e.g. a thin adhesive dressing, wherein the thickness of the adhesive layer is between 50 and 250 μm where it is thickest. The adhesive layer may thus have varying thickens or it may have a uniform thickness selected from values between 50 and 250 μm.

A dressing of the invention may in a preferred embodiment comprise an absorbing pad for the uptake of body fluids, especially wound exudates, so as to enable the wound dressing to keep a constant moist environment over the wound site, and at the same time avoiding maceration of the skin surrounding the wound.

According to still another embodiment of the invention the medical device is a wound dressing as above comprising an absorbent pad and where the thickness of the adhesive layer is between 50 and 300 μm where it is thickest. The adhesive layer may thus have varying thickness or it may have a uniform thickness selected from values between 50 and 300 μm.

An absorbent pad may be situated at the surface of the adhesive layer for contacting the wound or skin or between the adhesive layer and a backing.

A suitable foam material for use as a pad material for a dressing of the invention is e.g. a polyethylene foam, a polyurethane foam, a polyalkylene oxide and/or polyalkylene oxide siloxane foam.

An absorbent pad may comprise hydrocolloids, super absorbents, or foams or natural or synthetic materials which have extensive capacity to absorb body fluids, especially wound exudates. The absorbent pad may comprise an exudate distributing material. This renders it possible to utilise the areas of absorbent layer not being located right above the wound as well as the wetted surface of the absorbent layer will be enlarged and thus the evaporation through the backing layer will be enhanced.

The absorbent pad may be in the form of one or more layers, e.g. a multilayer, comprising layers of different absorption properties in order to optimize the absorption capacity of the absorbent layer. The absorbent pad may be in the form of a matrix structure, e.g. with incorporated particles. When the absorbent pad comprises a material capable of distributing the absorbed exudates, full utilisation of the absorption capacity in the dressing may be obtained.

The absorbent pad may comprise particles or fibres of any absorbent material known per se being suitable for use in wound care devices, e.g. polyacrylate, CMC, cellulose or derivatives thereof, gums, foam or alginate. A dressing of the invention may be produced in a manner known per se for applying an adhesive material onto a backing, e.g. laminating or dye casting or spreading the adhesive to a part of or the whole of one surface of the backing.

A dressing of the invention is optionally covered in part or fully by one or more release liners, or cover films to be removed before or during application. A protective cover or release liner may for instance be siliconized paper. It does not need to have the same contour as the dressing, and a number of dressings may be attached to a larger sheet of protective cover. The protective cover is not present during the use of the dressing of the invention and is therefore not an essential part of the invention. Furthermore, the dressing of the invention may comprise one or more "non touch" grip (s) known per se for applying the dressing to the skin without touching the adhesive layer. Such a non-touch grip is not present after application of the dressing. For larger dressings it is suitable to have 2 or 3 or even 4 "non-touch" grips.

Dressings comprising an absorbing pad or element for the uptake of body fluids, especially wound exudates, so as to enable the wound dressing to keep a constant moist environment over the wound site are described in WO 02/05737, U.S. Pat. No. 5,086,764, EP 641 553, WO 91/01706 and EP 236 104. The adhesive according to the present invention may replace the adhesive comprised in any of these known dressings.

By the invention it has been made possible to prepare dressings with the following properties:

A combined adhesive and backing layer with a thickness of 250 μm or above where it is thickest and having a moisture vapour transmission rate above 850 g/m$^2$/24 h, by selecting a backing layer having a moisture vapour transmission rate above 850 g/m$^2$/24 h and a layer of the adhesive composition of the invention comprising 5-30% w/w of a water absorbent hydrophilic agent.

A combined adhesive and backing layer having a moisture vapour transmission rate above 850 g/m$^2$/24 h and a water absorption below 75% w/w, by selecting a backing having a moisture vapour transmission rate above 850 g/m$^2$/24 h and a layer of the adhesive composition of the invention comprising 5-30% w/w of a water absorbent hydrophilic agent.

A combined adhesive and backing layer having a moisture vapour transmission rate above 850 g/m$^2$/4 h and an erosion of 0 mm after 4 hours, by selecting a backing having a moisture vapour transmission rate above 850 g/m$^2$/24 h and a layer of the adhesive composition of the invention comprising 5-30% w/w of a water absorbent hydrophilic agent.

For some uses it is very important that the adhesive composition has a high moisture vapour transmission rate and a high adsorption capacity but does note disintegrate or erode during use. One such use is as an adhesive used as a skin barrier in connection with an ostomy appliance. Another use is in connection with exudating wounds.

As may be seen from the experimental examples below, the erosion resistance of the adhesive of the invention decreases from 30% w/w to 40% w/w of water absorbent hydrophilic agent.

According to one embodiment of the invention, the medical device is an adhesive body side member for a two-piece ostomy appliance or an adhesive flange for a one-piece ostomy appliance where said adhesive body side member or said adhesive flange comprises a layer of the adhesive composition of the invention comprising 5-30% w/w, preferably 10-30% w/w, of water absorbent hydrophilic agent(s) attached to a backing layer. According to this embodiment of the invention, the thickness of the adhesive layer is between 0.5 and 1.5 mm where it is thickest. The backing used in connection with ostomy appliances may be a non vapour permeable backing or a permeable backing.

For some devices a high fluid absorption (e.g ostomy appliances) or long term use (days) may be the primary goal, while the erosion resistance and the hardness of the adhesive is still kept at an acceptable level for the particular use.

As may be seen from the experimental section, erosion and the hardness (the modulus) of the adhesive of the invention increases dramatically when increasing the amount of water absorbent hydrophilic agent from 40 to 50% w/w.

For uses requiring a high fluid absorption or long term use (days) it is preferred to use an adhesive of the invention comprising 30-40% w/w, preferably 30-35% w/w or 35-40% w/w of a water absorbent hydrophilic agent.

According to the invention, it has been made possible to prepare a medical device comprising a backing layer and a layer of adhesive wherein the moisture vapour transmission rate of the combined backing layer and adhesive layer is above 1350 g/m$^2$/24 h by selecting a backing layer having a moisture vapour transmission rate above 1350 g/m$^2$/24 h and a layer of the adhesive composition of the invention, 0.3 mm or above in thickness, comprising 30-40% w/w of a water absorbent hydrophilic agent.

According to the invention, it has been made possible to prepare a medical device comprising a backing and a layer of adhesive wherein the moisture vapour transmission rate of the combined backing layer and adhesive layer is above 1350 g/m$^2$/24 h and a water absorption above 75% w/w by selecting a backing layer having a moisture vapour transmission rate above 1350 g/m²/24 h and a layer of the adhesive composition of the invention comprising 30-40% w/w of a water absorbent hydrophilic agent.

The invention therefore relates to a medical device as above wherein said pressure sensitive adhesive comprises 30-40% w/w of water absorbent hydrophilic agent(s).

In one embodiment the medical device is an adhesive body side member for a two-piece ostomy appliance or an adhesive flange for a one-piece ostomy appliance where said adhesive body side member or said adhesive flange comprises a layer of the adhesive of the invention attached to a backing layer, said adhesive composition comprising 30-40% w/w, preferably 30-35% w/w or 35-40% w/w, of water absorbent hydrophilic agent(s). According to this embodiment of the invention the thickness of the adhesive layer is between 0.5 and 1.5 mm where it is thickest.

In another embodiment, the medical device is a dressing for exudating wounds comprising a layer of the adhesive composition of the invention attached to a backing layer, said adhesive composition comprising 30-40% w/w, preferably 30-35% w/w or 35-40% w/w, of water absorbent hydrophilic agent(s). According to this embodiment, the thickness of the adhesive layer where it is thickest is between 200 µm and 1 mm.

An adhesive composition comprising 30-40% w/w, preferably 30-35% w/w or 35-40% w/w, of a water absorbent hydrophilic agent may also be suitable for attaching medical devices which are worn on the skin for long time (days) and which contain and element(s) occluding moisture transmission partly or completely when attached to the skin. Examples of such devices are prostheses, and measuring instruments or electrical devices attached to the skin, or devices comprising a non vapour permeable backing.

The invention therefore relates to a medical device as above comprising element(s) inhibiting water vapour transmission and a layer of the adhesive composition of the invention comprising 30-40% w/w of water absorbent hydrophilic agent(s).

In one particular embodiment of the invention, the medical device comprises element(s) inhibiting water vapour transmission where said element(s) is embedded in an adhesive composition of the invention comprising 30-40% w/w of a water absorbent hydrophilic agent.

The invention therefore relates to a medical device comprising a microelectronic system and comprising a layer of said adhesive composition comprising 30-40% w/w of water absorbent hydrophilic agent(s).

The invention also relates to a medical device comprising a microelectronic system wherein said microelectronic system is embedded in an adhesive body of said adhesive composition comprising 30-40% w/w of water absorbent hydrophilic agent.

The microelectronic system may comprise components selected from communication component(s), CPU, power source, storage component(s), transducer component(s), actuator component(s) and mechanical and/or electrical interconnection between the components.

The microelectronic system may be a system enabling wireless communication.

The transducer may have a detecting element selected from electrodes (polar, bipolar), a pressure sensor, a needle with an electrode, an accelerometer, a photo detector, a microphone, ISFET, an NTC resistor, a band gab detector, an ion membrane, an enzyme detector or a condenser.

Suitably, the transducer has a non-invasive detecting element, such as electrodes, e.g. steel electrodes. According to another embodiment the transducer has an invasive detecting element, such as a needle containing an electrode.

A typical example of a medical device comprising microelectronic systems element(s) is a power source, a measuring instrument or a therapeutic instrument, which is attached to the skin, such as devices useful for measuring ECG (Electro CardioGraphy), EMG (Electro MyoGraphy), EEG (Electro EncephaloGraphy), blood glucose, pulse, blood pressure, pH, and oxygen, or a battery.

Such instruments are known in the art and they are usually attached to the skin by a pressure sensitive adhesive.

Examples of such devices are described in e.g. WO 03/065926, U.S. Pat. No. 5,054,488, U.S. Pat. No. 5,458,124, U.S. Pat. No. 6,372,951, U.S. Pat. No. 6,385,473, WO 99/59465 and US application No. 2003/0009097. An adhesive in accordance with the present invention may replace the adhesive used for attaching these devices to the skin. The adhesive surface of the medical device as above, which is to be attached to the skin, is optionally covered in part or fully by one or more release liners, which are removed before or during application. The release liner may be of any material known to be useful as a release liner for medical devices.

Flexibility in the adhesive part of a medical device is often achieved by device design, such as beveling or patterning in the adhesive.

An ostomy appliance of the invention may be in the form of a wafer forming part of a two-piece appliance or in the form of a one-piece appliance comprising a collecting bag for collecting the material emerging from the stoma. A separate collecting bag may be attached to the wafer by any manner known per se, e.g. through mechanical coupling using a coupling ring or through use of adhesive flanges.

A wafer for an ostomy appliance of the invention also typically comprises a water vapour permeable and water impervious backing layer and a release liner as discussed above.

An ostomy appliance of the invention may be produced in a manner known per se from materials conventionally used for the preparation of ostomy appliances.

The dressing of the invention may also be a dressing suitable for bandaging purposes and for protection of skin around body openings, especially around stomas, or for sealing around a medical device attached to the skin, i.e an ostomy appliance or any other medical device.

In a further embodiment, the invention relates to prosthesis of the type to be adhered to the skin of the user, such as a breast prosthesis comprising an adhesive construction according to the invention.

The invention also relates to a urine collecting device comprising an adhesive as described above.

Urine collecting devices according to the invention may be in the form of uri-sheaths.

EXPERIMENTAL

The following materials were used to prepare pressure sensitive adhesives according to the invention and pressure sensitive adhesive compositions for comparison:

Aquasorb A800, a cross-linked carboxymentyl cellulose from Aqualon.

ACX003, allyl-terminated polyether (poly propylene oxide) viscosity 16 Pa·s from Kaneka.

Catalyst Pt-VTS. Pt-VTS is Pt-divinyl teteramethyl disiloxane in IPA (Pt 3.0 wt %).

CR600, poly-alkyl hydrogen siloxane curing agents available from Kaneka.

Chain extender Mod700, poly-alkyl hydrogen siloxane chain extender from Hanse Chemie Comparative Example 1

Preparation of Cross-Linked Polypropylene Oxide Based Adhesive

The ingredients listed in tables 1 and 2 were used to prepare cross-linked polypropylene oxide based adhesives as described in WO 2005/032401.

TABLE 1

| Ingredients in w/w % | |
|---|---|
| | C1 |
| Polymer AC003 | 96.50 |
| Cross linker CR600 | 3.40 |
| Catalyst Pt-VTS | 0.09 |

TABLE 2

| Ingredients in w/w % | |
|---|---|
| | C2 |
| Polymer AC003 | 95.83 |
| Cross linker CR600 | 3.80 |
| Chain extender Mod700 | 0.28 |
| Catalyst Pt-VTS | 0.09 |

The ingredients were mixed using a lab static mixer at 5 ml/min. using a 10.7/32M mixer (Sulzer) at room temperature. The mixture was formed into sheet stock materials having a thickness of approximately 0.3 mm and 1 mm by compression moulding the adhesive mass at approximately 100° C. between one sheet of silicone release paper and a 30 μm PU film (Inspire 2301 from Intelicoat) for 30 seconds. The plates were allowed to finish reaction in an oven at 100° C. for 30 minutes. The resultant flat plate was cut into the desired shapes.

Example 1

Preparation of an Adhesive Based on Cross-Linked Polypropylene Oxide Comprising Aquasorb A800

The adhesive compositions were prepared by mixing the desired amount of the un-reacted C1 mixture (see comparative example 1) and the desired amount of Aquasorb A800 (see table 3 below) in a beaker and mixing by hand with a spetula for 5 min at room temperature. The resulting adhesive compositions was formed into sheet stock materials having a thickness of approximately 0.3 and 1 mm by compression moulding the adhesive mass at approximately 100° C. and 100 Bar between one sheet of silicone release paper and a 30 μm PU film (Inspire 2301 from Intelicoat) for 30 seconds. The plates were allowed to finish reaction in an oven at 100° C. for 30 minutes. The resultant flat plate was cut into the desired shapes.

TABLE 3

| Polypropylene oxide/hydrocolloid adhesive. | | | | | | |
|---|---|---|---|---|---|---|
| | S0 | S1 | S2 | S3 | S4 | S5 |
| C1 (% w/w) | 97.2 | 90 | 80 | 70 | 60 | 50 |
| Aquasorb A800 (% w/w) | 2.8 | 10 | 20 | 30 | 40 | 50 |

S5 was found difficult to prepare due to high viscosity of the mixture and the sample obtained contained many air bubbles.

Example 2

Preparation of an Adhesive Based on Cross-Linked Polypropylene Oxide Comprising Aquasorb A800

The adhesive compositions were prepared by mixing the desired amount of the un-reacted C2 mixture (see comparative example 1) and the desired amount of Aquasorb A800 (see table 2 below) in a beaker and mixing by hand with a spetula for 5 min at room temperature. The resulting adhesive compositions was formed into sheet stock materials having a thickness of approximately 0.3 and 1 mm by compression moulding the adhesive mass at approximately 100° C. and 100 Bar between one sheet of silicone release paper and a 30 μm PU film (Inspire 2301 from Intelicoat) for 30 seconds. The plates were allowed to finish reaction in an oven at 100° C. for 30 minutes. The resultant flat plate was cut into the desired shapes.

TABLE 4

| Polypropylene oxide/hydrocolloid adhesive. | | | | | |
|---|---|---|---|---|---|
| | X1 | X2 | X3 | X4 | X5 |
| C2 | 90 | 80 | 70 | 60 | 50 |
| Aquasorb A800 | 10 | 20 | 30 | 40 | 50 |

X5 was found difficult to prepare due to high viscosity of the mixture and the sample obtained contained many air bubbles.

Example 3

Using the methods described below, the water absorption and the moisture vapour transmission rate was measured for the adhesives in comparative example 1 and the adhesives in example 1-2.

Determination of Water Absorption

Pieces of adhesive of 1×25×25 mm were immersed in a 0.9% NaCl (w/w) solution in demineralised water at 37° C. The samples was removed and carefully dripped dry and weighed after 30, 60, 90, 120, 240, and 1440 minutes. The percentage change in weight is recorded. The 1440 minutes average results from duplicates appear from the table below.

Determination of Moisture Vapour Transmission Rate (MVTR)

MVTR is measured in grams per square meter (g/m2) over a 24 hours period using an inverted cup method.

A container that is water and water vapour impermeable, but with an opening. 20 ml of 0.9% NaCl (w/w) solution in demineralised water is placed in the container and the opening is sealed with the test adhesive film of 0.3 mm thickness on the PU backing (Inspire 2301 from Intelicoat) with the adhesive layer on the inside. The container, with a duplicate, are each weighed and placed into an electrically heated humidity cabinet. The cabinet is maintained at 37° C., 15% relative humidity for 24 hours. After this the containers are removed, allowed to cool for 1 hour and reweighed.

The MVTR is calculated from the mean loss in weight and the area of the opening in the top of each container as g/m²/24 hours.

Results

The results obtained are presented in the tables below:

TABLE 5

Adhesives based on polypropyleneoxide.

| | Adhesive | MVTR | |
|---|---|---|---|
| Sample name | Aquasorb A800 w/w % | g/m²/24 hours | Water abs. % w/w |
| C1 | 0% A800 | 759 | 4 |
| C2 | 0% A800 | 660 | 5 |
| S0 | 2.8% A800 | 933 | 12 |
| S1 | 10% A800 | 1275 | 31 |
| S2 | 20% A800 | 1344 | 45 |
| S3 | 30% A800 | 1367 | 83 |
| S4 | 40% A800 | 1887 | 373 |
| S5 | 50% A800 | nm | nm | nm = not measured

Sample S5 was not measured since samples contained may air bubbles and holes which would affect the measurement.

The invention compositions S1 to S4 all show very high vapour permeability and high water absorption. Surprisingly high increase in water permeability and water absorption are achieved by increasing the amount of water absorbent hydrophilic agent from 0% by weight to just 2.5 and 10% by weight.

Example 4

Sample Preparation for Erosion and Rheology Testing

Approximately 3 gram of the adhesive composition is transferred to silicone release liner. An approximately 1.0 mm thick adhesive plate is made by compression moulding the adhesive mass at approximately 100° C. between two sheets of silicone release paper for 10 s. The plates were allowed to finish reaction in an oven at 100° C. for 30 minutes.

The elastic modulus G' was measured as follows:

A disc of the adhesive having a thickness of 1 mm with 25 mm diameter is cut out from the plate for rheology measurements. The rheometer RheoStress RS600 rheometer from Thermo Electron (Karlsruhe) is used. The geometry applied is parallel plates 25 mm. The upper plate was adjusted so that there is a normal force of approximately 5N. A frequency sweep measurement is performed at a constant temperature of 32° C. starting at 100 Hz going down to 0.01 Hz. The rheometer is kept in strain-controlled mode, and the strain applied is 1%, which is in the linear regime for the applied materials. The rheological data obtained was as follows:

TABLE 6

| | G' 0.01/s | Pa |
|---|---|---|
| C1 | 0% A800 | 1340 |
| S1 | 10% A800 | 1600 |
| S2 | 20% A800 | 2140 |
| S3 | 30% A800 | 3800 |
| S4 | 40% A800 | 29000 |
| S5 | 50% A800 | 348800 |

Using an adhesive based on cross-linked polypropylene oxide and increasing amounts of water absorbent hydrophilic agent it has been established that a considerable (more than 10 times) increase in modulus takes place from the adhesive comprising 40% hydrocolloid to the adhesive comprising 50% hydrocolloid.

With the adhesives of the invention it is possible to provide an adhesive, which has high moisture vapour transmission rate and a high absorption capacity with an amount of hydrocolloid, which is considerably lower than the amount giving a hard an uncomfortable adhesive.

Example 5

Test for Erosion Resistance

The erosion of the adhesive of the invention as a function of the amount of hydrocolloid was measured as follows using a sample as prepared in example 4:

A disk of the adhesive having a thickness of 1 mm, an outer diameter of 50 mm and a hole of diameter of 15 mm was coated on the top surface with an impermeable film of LDPE. The exposed surface was attached to the surface of a petri dish. The adhesive and dish were left at 37° C. for 24 hrs. Then the dish was filled with 0.9% NaCl demineralised water. The whole adhesive specimen was covered by water. The dish was then covered with a plastic sheet and left at 37° C. for 24 hrs. Erosion was shown by the distance of water ingress, in mm, at the inner, and an outer edges of the sample, measured at 4 and 24 hrs. The results show the 4 hrs results. The erosion after 4 hours were as follows:

TABLE 7

| Sample | % Aquasorb A800 | Erosion outer side (mm) | Erosion inner side (mm) |
|---|---|---|---|
| X1 | 10 | 0 | 0 |
| X2 | 20 | 0 | 0 |
| X3 | 30 | 0 | 0 |
| X4 | 40 | 3 | 2 |
| X5 | 50 | * | * |

* Sample too irregular to measure

As it appears from the results there is a change in erosion resistance between 30 and 40% hydrocolloid.

The invention claimed is:

1. A pressure sensitive adhesive composition consisting of a continuous phase comprising cross-linked polyalkyleneoxide polymer and a discontinuous phase comprising at least one water absorbent hydrophilic agent, characterized in that
   a) the water absorbent hydrophilic agent or agents are present in an amount between 1 and 40% w/w of the total adhesive composition; and
   b) the continuous phase comprises the reaction product (X) of:
      (i) a polyalkyleneoxide polymer having one or more unsaturated end groups, and where more than 90% w/w of the polyalkylene oxide polymer consists of polymerised alkyleneoxide moieties having three or more carbon atoms, and
      (ii) an organosiloxane comprising one or more Si—H groups, carried out in the presence of an addition reaction catalyst.

2. The pressure sensitive adhesive according to claim 1 wherein the total amount of water absorbent hydrophilic agent or agents is 5-40% w/w, of the total adhesive composition.

3. The pressure sensitive adhesive composition according to claim 2 wherein the amount of water absorbent hydrophilic agent or agents is 5-30% w/w of the total adhesive composition.

4. The pressure sensitive adhesive composition according to claim 1 wherein the continuous phase comprises the reaction product (Y) of:
(ia) a polyalkyleneoxide polymer having at least two unsaturated end groups, and where more than 90% w/w of the polyalkyleneoxide polymer consists of polymerised alkyleneoxide moities having three or more carbon atoms, (iia) a polysiloxane cross-linking agent comprising 3 or more Si—H groups and optionally
(ilia) a polysiloxane chain extender comprising up to 2 Si—H groups, carried out in the presence of an addition reaction catalyst.

5. The adhesive composition according to claim 1 wherein the polyalkylene oxide polymer is polypropyleneoxide.

6. The pressure sensitive adhesive according to claim 1 wherein at least 60% w/w of the continuous phase consists of said reaction product.

7. The pressure sensitive adhesive composition according to claim 1 wherein the water absorbent hydrophilic agent or agents are selected from the group consisting of water swellable (non-water soluble) hydrocolloids and water soluble hydrocolloids.

8. The pressure sensitive adhesive composition according to claim 7 wherein the hydrocolloid is selected from the group consisting of hydrocolloids of cross-linked polymers.

9. The pressure sensitive adhesive composition according to claim 1 wherein the hydrocolloids have a particle size less than 20 microns.

10. The pressure sensitive adhesive composition according to claim 9 wherein the hydrocolloids have a particle size below 5 microns.

11. The pressure sensitive adhesive composition according to claim 9 wherein the hydrocolloids have a particle size below 2 microns.

12. A medical device comprising a pressure sensitive adhesive composition consisting of a continuous phase comprising cross-linked polyalkyleneoxide polymer and a discontinuous phase comprising at least one water absorbent hydrophilic agent characterized in that
a) the water absorbent hydrophilic agent or agents are present in an amount between 1 and 40% w/w of the total adhesive composition; and
b) the continuous phase comprises the reaction product (X) of:
(i) a polyalkyleneoxide polymer having one or more unsaturated end groups, and where more than 90% w/w of the polyalkylene oxide polymer consist of polymerised alkyleneoxide moities having three or more carbon atoms, and
(ii) an organosiloxane comprising one or more Si—H groups, carried out in the presence of an addition reaction catalyst.

13. The medical device according to claim 12 comprising elements inhibiting water vapour transmission and comprising a layer of said adhesive composition comprising 30-40% w/w of water absorbent hydrophilic agent or agents.

14. The medical device according to claim 12 comprising elements inhibiting water vapour transmission where said elements are embedded in an adhesive body of said adhesive composition comprising 30-40% w/w of water absorbent hydrophilic agent or agents.

15. The medical device according to claim 12 comprising one or more microelectronic systems and comprising a layer of said adhesive composition comprising 30-40% w/w of water absorbent hydrophilic agent or agents.

16. The adhesive device according to claim 15, wherein the microelectronic systems comprise components selected from the group comprising communication components, CPU, power source, storage components, transducer components, actuator components and mechanical and electrical interconnection between the components.

17. The adhesive device according to claim 16, wherein the transducer has a detecting element selected from the group consisting of electrodes (polar, bipolar), a pressure sensor, a needle with an electrode, an accelerometer, a photo detector, a microphone, ISFET, an NTC resistor, a band gab detector, an ion membrane, an enzyme detector and a condenser.

18. The adhesive device according to claim 17, wherein the transducer has a non-invasive detecting element.

19. The adhesive device according to claim 17, wherein the transducer has an invasive detecting element comprising a needle containing an electrode.

20. The adhesive device according to claim 15, wherein the microelectronic system is a system enabling wireless communication.

21. The medical device according to claim 12 comprising one or more microelectronic systems wherein said microelectronic systems are embedded in an adhesive body of said adhesive composition comprising 30-40% w/w of water absorbent hydrophilic agent or agents.

22. A medical device comprising a pressure sensitive adhesive composition a continuous phase comprising cross-linked polyalkyleneoxide polymer and a discontinuous phase comprising at least one water absorbent hydrophilic agent characterized in that
a) the water absorbent hydrophilic agent or are present in an amount between 1 and 40% w/w of the total adhesive composition; and
b) the continuous phase comprises the reaction product (X) of:
(i) a polyalkyleneoxide polymer having one or more unsaturated end groups, and where more than 90% w/w of the polyalkylene oxide polymer consist of polymerised alkyleneoxide moities having three or more carbon atoms, and
(ii) an organosiloxane comprising one or more Si—H groups, carried out in the presence of an addition reaction catalyst and a backing layer.

23. The medical device according to claim 22 wherein the backing layer is non-vapour permeable.

24. The medical device according to claim 22 wherein the backing layer is water vapour permeable and have a moisture vapour transmission rate above 500 g/m$^2$/24 h.

25. The medical device according to claim 22, wherein the medical device comprises the adhesive composition in the form of a layer attached to said backing and wherein the adhesive composition comprises 5-30% w/w of at least one water absorbent hydrophilic agent and the backing layer has a moisture vapour transmission rate above 500 g/m2/24 h.

26. The medical device according to claim 25 wherein the medical device is a dressing.

27. The medical device according to claim 26 wherein the dressing is a wound dressing comprising an absorbent pad and the thickness of the adhesive layer is between 50 and 300 µm where it is thickest.

28. The medical device according to claim 25, wherein the adhesive composition comprises 5-25% w/w of water absorbent hydrophilic agent or agents.

29. The medical device according to claim 28, wherein the adhesive composition comprises 5-15% w/w of water absorbent hydrophilic agent or agents.

30. The medical device according to claim 25 wherein the thickness of the adhesive layer is between 50 and 250 µm where it is thickest.

31. The medical device according to claim 22, wherein the medical device is an adhesive body side member for a two-piece ostomy appliance or an adhesive flange for a one-piece ostomy appliance where said adhesive body side member or said adhesive flange comprises a layer of said adhesive composition comprising 5-30% w/w of at least one water absorbent hydrophilic agent attached to said backing layer.

32. The medical device according to claim 31 wherein the thickness of the adhesive layer is between 0.5 and 1.5 mm where it is thickest.

33. The medical device according to claim 22, wherein said pressure sensitive adhesive comprises 30-40% w/w of water absorbent hydrophilic agent or agents.

34. The medical device according to claim 22, wherein where the medical device is an adhesive body side member for a two-piece ostomy appliance or an adhesive flange for a one-piece ostomy appliance where said adhesive body side member or said adhesive flange comprises a layer of said adhesive composition comprising 30-40% w/w of at least one water absorbent hydrophilic agent attached to said backing layer.

35. The medical device according to claim 22 where the medical device is a dressing for exudating wounds comprising a layer of said adhesive composition attached to said backing layer, said adhesive composition comprising 30-40% w/w of at least one water absorbent hydrophilic agent and the backing layer has a moisture vapour transmission rate above 500 g/m2/24 h.

36. The medical device according to claim 35 wherein the thickness of the adhesive layer is between 200 µm and 1 mm where it is thickest.

37. The pressure sensitive adhesive composition according to claim 8, wherein the hydrocolloid comprises cross-linked carboxymethyl cellulose.

38. The adhesive device according to claim 18, wherein the non-invasive detecting element of the transducer is an electrode.

* * * * *